United States Patent
Everingham et al.

(10) Patent No.: US 9,861,516 B2
(45) Date of Patent: Jan. 9, 2018

(54) OCCLUSIVE PLUG

(71) Applicant: OI MEDICAL LIMITED, Sheffield (GB)

(72) Inventors: John Sanders Everingham, Sheffield (GB); Gilbert Marcus Filshie, Mapperley Park (GB); Bernard Sweeney, Thames Ditton (GB); Adam Laszlo Magos, Barnet (GB)

(73) Assignee: O.I. MEDICAL LIMITED, Sheffield (GB)

( * ) Notice: Subject to any disclaimer, the term of this patent is extended or adjusted under 35 U.S.C. 154(b) by 529 days.

(21) Appl. No.: 14/378,736

(22) PCT Filed: Feb. 20, 2013

(86) PCT No.: PCT/GB2013/000070
§ 371 (c)(1),
(2) Date: Aug. 14, 2014

(87) PCT Pub. No.: WO2013/124612
PCT Pub. Date: Aug. 29, 2013

(65) Prior Publication Data
US 2015/0040914 A1    Feb. 12, 2015

(30) Foreign Application Priority Data
Feb. 21, 2012   (GB) .................................. 1202935.1

(51) Int. Cl.
*A61F 6/22*    (2006.01)

(52) U.S. Cl.
CPC ................. *A61F 6/225* (2013.01); *A61F 6/22* (2013.01)

(58) Field of Classification Search
CPC ................................... A61F 6/225; A61F 6/22
USPC ............. 606/119; 604/19, 48, 500, 514, 515
See application file for complete search history.

(56) References Cited

U.S. PATENT DOCUMENTS

| | | | |
|---|---|---|---|
| 7,846,160 B2 | 12/2010 | Payne et al. | |
| 2004/0153092 A1 | 8/2004 | Beger et al. | |
| 2004/0204720 A1 | 10/2004 | Harrington | |
| 2005/0217680 A1 | 10/2005 | Callister et al. | |
| 2010/0006105 A1* | 1/2010 | Carter ..................... | A61F 6/225 128/831 |
| 2011/0174312 A1* | 7/2011 | Everingham ........... | A61F 6/225 128/831 |

FOREIGN PATENT DOCUMENTS

| | | | | |
|---|---|---|---|---|
| EP | 1800633 A1 * | 6/2007 | ....... | A61B 17/12022 |
| WO | 9712569 A1 | 4/1997 | | |
| WO | 2004098469 A1 | 11/2004 | | |
| WO | 2007072004 A1 | 6/2007 | | |
| WO | 20100043857 A2 | 4/2010 | | |

* cited by examiner

Primary Examiner — Tarla Patel
(74) Attorney, Agent, or Firm — King & Schickli, PLLC

(57) ABSTRACT

A plug (1) for use in occluding a fallopian tube hysterescopically, said plug comprising:
an elongate body (2) having an external thread (3), characterized in that:
said body is fenestrated (6,17; 7,18; 8,19).

35 Claims, 2 Drawing Sheets

OCCLUSIVE PLUG

FIELD OF THE INVENTION

This invention relates to an occlusive plug for use in occluding a fallopian tube hysteroscopically as a means of sterilisation.

BACKGROUND OF THE INVENTION

The principle of using a threaded plug to be retained within the fallopian tube is known from WO 97/12569 which describes a plug in the form of an elongate body having an external thread, which plug, upon rotation, screws itself into the fallopian tube, the plug being self-retaining, and effective when in situ for purposes of sterilisation. Clearly the plug dimensions need to be selected according to the species to be sterilised, with the dual requirement of security against migration which might be caused by muscular tubal peristalsis, yet an ability to remove the plug at a later date should it be required to reverse the sterilisation procedure.

In WO 2007/072004 is described an improved plug less prone to ejection and hence sterilisation failure, by providing a thread with a large root length and a large pitch. The proposal was to produce the plug in implantable grade polyethylene and various dimensions and ratios were advanced for thread forms to meet the practical requirements.

In PCT/GB2009/002450 are described several embodiments of plug proposals intended to provide enhanced resistance to migration and resultant loss of effectiveness.

OBJECT OF THE INVENTION

A basic object of the present invention is the provision of a further improved plug.

SUMMARY OF THE INVENTION

According to one aspect of the present invention, there is provided a plug for use in occluding a fallopian tube hysteroscopically comprising an elongate body having an external thread, characterized in that the body is fenestrated.

Preferably, the thread is non-fenestrated.

Other aspects are as set out in the claims herein.

Advantages of the Invention

As with the proposal of PCT/GB2009/002450, the fenestration enables endosalpinx and muscular tissue growth into and/or through the fenestrations in the body to aid anchorage of the plug occluding the lumen but fenestration of the body is not only achievable with reduced difficulty, compared with fenestration of the threads, but also avoids weakening of the threads by the introduction of fenestration apertures. Also as before, the provision of fenestrations (in the body) would also reduce the possibility of post operative migration of the plug. Such tissue growth would of course make the plug more difficult to remove should reversal of sterilisation be required, at some future date, but it is believed the lumen would quickly regenerate.

BRIEF DESCRIPTION OF THE DRAWINGS

For a better understanding of the invention and to show how the same may be carried into effect, there will now be described by way of example only, specific embodiments, methods and processes according to the present invention with reference to the accompanying drawings.

Specific embodiment plugs in accordance with the invention are shown in greater detail, by way of example, in the accompanying drawings, in which.

DETAILED DESCRIPTION OF THE EMBODIMENTS

Figure 1:
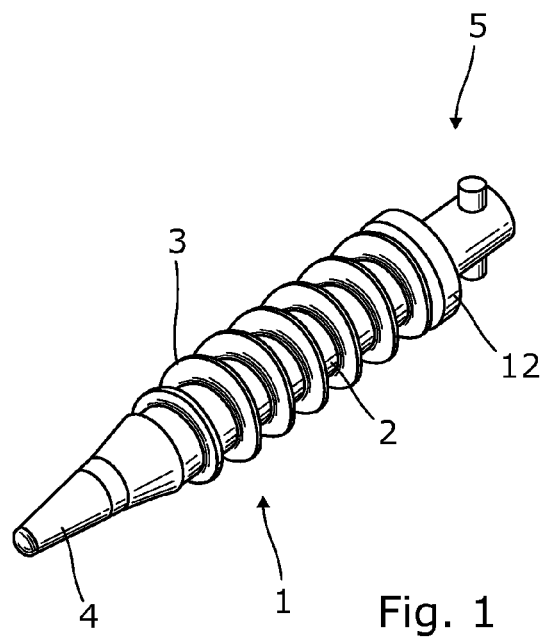
FIG. 1 is a perspective view to size, of a plug.

There will now be described by way of example a specific mode contemplated by the inventors. In the following description numerous specific details are set forth in order to provide a thorough understanding. It will be apparent however, to one skilled in the art, that the present invention may be practiced without limitation to these specific details. In other instances, well known methods and structures have not been described in detail so as not to unnecessarily obscure the description.

Referring to FIGS. 1 to 4 herein, there is illustrated schematically a first specific embodiment plug for use in occluding a fallopian tube hysteroscopically.

The plug 1 comprises an elongate body 2 having a helical screw thread 3 extending along a length of said body; at a front end of said body, a tapered nose 4; and at a rear end of said body a drive head 5 for driving the plug along a fallopian tube using a drive tool.

Plug body 2 comprises a plurality of fenestrations 6, 17; 7, 18; 8, 19, distributed along a length of the body. In the best mode, the fenestrations are in the form of a through-apertures extending along a diameter of the substantially cylindrical body, each said aperture comprising a pair of rectangular recesses or troughs, which connect to each other within said body, thereby forming a through passage.

Each said fenestration preferably has a depth as measured from an outer surface of the cylindrical body, extending between 1.65 and 1.85 mm into the body, and preferably a pair of connected fenestrations linked to form a passage through the body to a depth of 1.75 mm; a width in the range 0.51 mm to 0.55 mm, and preferably 0.53 mm, and a length of 0.711 mm to 0.911 mm, and preferably 0.811 mm.

A pair of said fenestrations are preferably arranged 180° opposite each other, on opposite sides of the substantially cylindrical body, but offset in the axial direction, such that one side of a first fenestration is adjacent to a side of a second fenestration, thereby providing an intersection between the pair of opposite fenestrations, creating a passage through the centre of the substantially cylindrical body.

Each fenestration extends radially into the body, and in a preferred embodiment, each fenestration is bisected by a plane which passes through a main central axis of the substantially cylindrical body.

However in other embodiments, the fenestrated troughs may be offset from each other, and offset relative to a plane bisecting the body along its main central axis. In other embodiments, the fenestrations need not necessarily form passages through the central body, but may be formed as a plurality of "blind" holes in the central body.

In a further embodiment, there may be provided a plurality of blind holes, troughs or fenestrations, arranged in a helical pattern around the outer circumference of the central body, positioned between the peaks of the adjacent thread.

Figure 3:
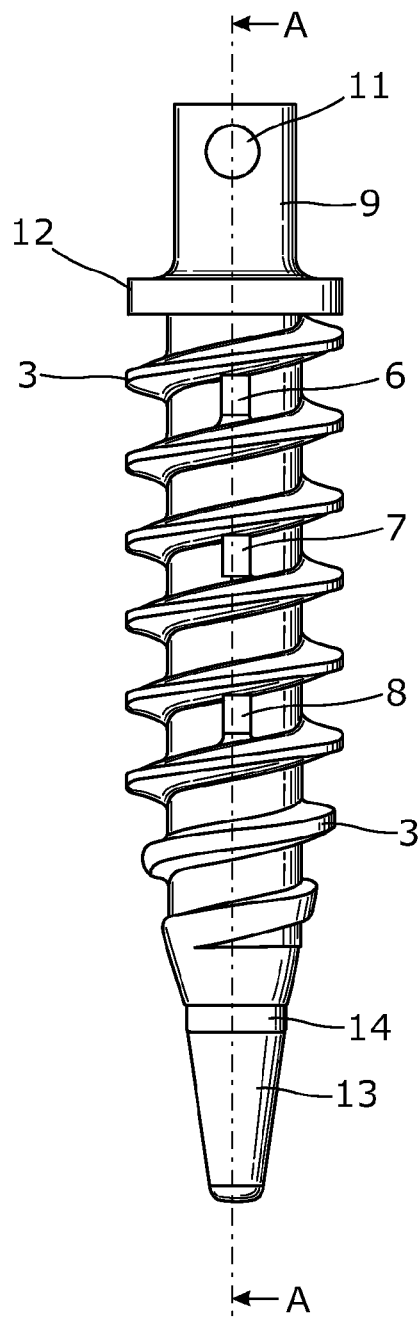
FIG. 3 is also an enlarged side elevation of the plug of FIG. 1, but after rotation through 90° compared to FIG. 2.
Figure 4:
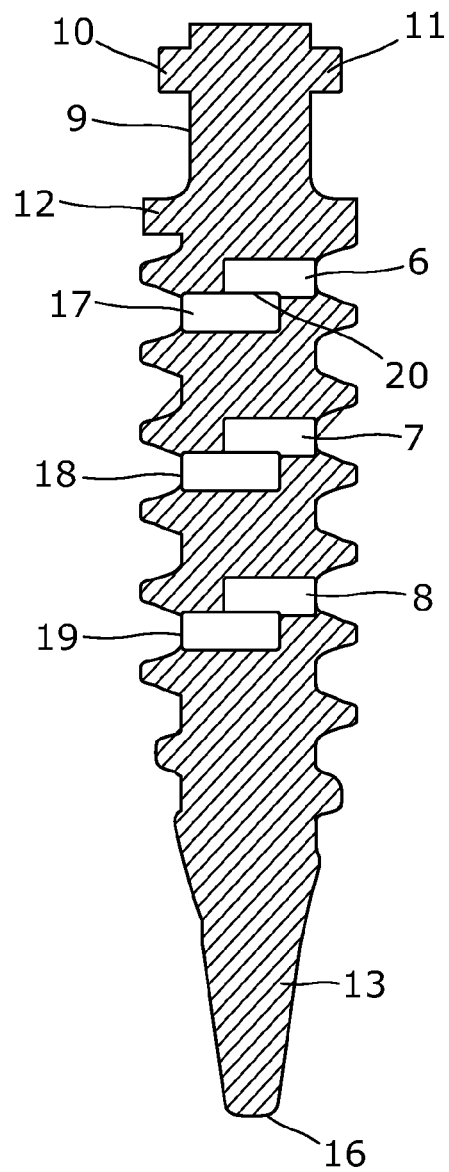
FIG. 4 is a section on the line A-A of FIG. 3.

In the best mode, there are three pairs of fenestrations, each providing a passage through the centre of the cylindrical body, said passages spaced at regular equal intervals along a length of said body as shown in FIGS. 3 and 4 herein. Three passages, each comprising a pair of fenestrations, pits or troughs are provided spaced apart axially along a length of the body.

Figure 2:
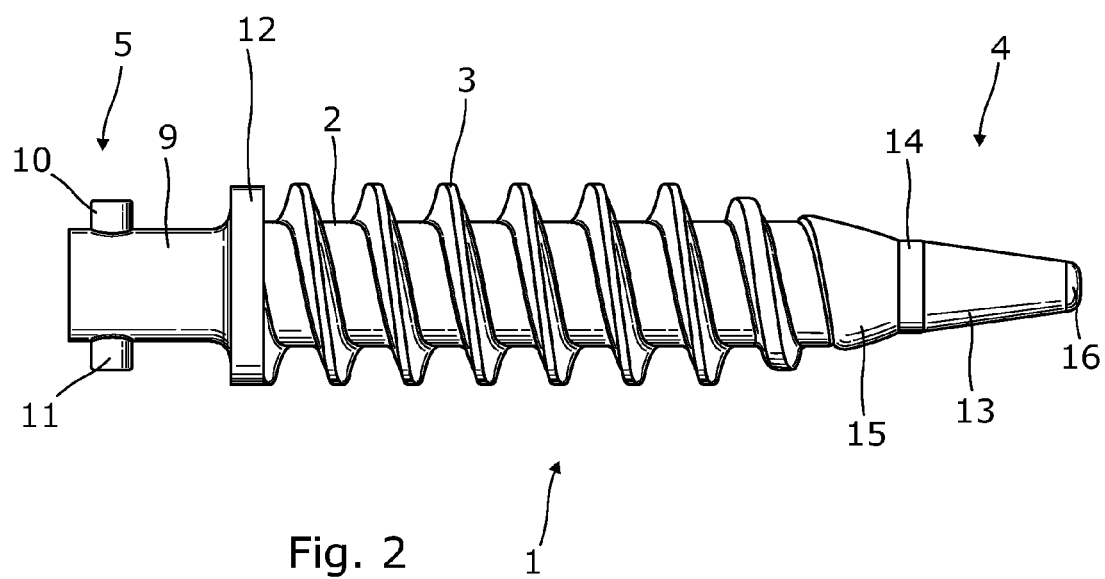
FIG. 2 is an enlarged side elevation of the plug of FIG. 1.

Referring to FIG. 2 herein, the rear end of the plug comprises a substantially cylindrical portion having a pair of lugs 10, 11 protruding radially outwards, forming a bayonet type end for insertion into a bayonet socket of a corresponding applicator. This enables the plug to be driven in either a clockwise or anticlockwise direction for insertion into or removal from a fallopian tube.

Referring to FIG. 3 herein, there is an illustrated schematically the embodiment plug, viewed with the plug rotated 90° relative to the view of FIG. 2 herein. The plurality of fenestrations 6-8 are shown in side view. The openings of the fenestrations on the surface of the body are positioned between adjacent turns of the helical thread 3.

The helical thread 3 comprises a spiral ridge winding around and projecting from the substantially cylindrical central body 2. In a preferred embodiment, the thread has a length in the range of 13.2 mm to 14.0 mm and preferably around 13.6 mm, and preferably there are between 6 and 7 full turns of the thread, and preferably 7 full turns, along the length of the body.

Towards the nose end, the thread is tapered over the first one or two turns, so as to allow easier insertion into a fallopian tube.

At a rear end of the plug is provided drive head 5. The drive head 5 comprises a substantially cylindrical portion 9, and towards a rear end of the cylindrical portion, a pair of protruding substantially cylindrical lugs 10, 11. Between the drive head and the thread, is provided a cylindrical collar 12 having an outside diameter substantially equal to that of an external diameter of the thread, the collar separating the drive head portion from the main threaded part of the plug.

At a front end of the plug, the nose portion 4 comprises a first tapered frusto-conical section 13 having a first and relatively shallow angled taper with respect to a main central axis of the body, a rear end of the first frusto-conical section 13 being connected to a front end of a second frusto conical section 14, the second frusto conical section having a second and greater angle of taper than the first frusto conical section, and a rear portion of the second frusto conical section 14 connecting to a front portion of a third frusto conical section 15, the third frusto conically section having a greater angle of taper relative to a main central axis of the plug, than the first and second frusto conical sections, the overall effect being that the nose has initially a long shallow taper, leading to a section of greater diameter, and greater taper angle and then on to the main diameter of the body section. The nose section leads smoothly to the start of the diameter of the tapered thread portion at the front end of the threaded section of the plug, so that in use as the plug is rotated within a fallopian tube, the fallopian tube experiences a gentle expansion, thereby facilitating a gentle insertion of the plug, minimizing trauma.

A front end of the nose is provided with a domed or hemispherical potion 16, having a smooth outer surface, providing a relatively blunt tip to the plug.

Referring to FIG. 4 herein, there is illustrated schematically in cross sectional view along the section "A-A" in FIG. 3 herein. Shown in a cut away view are three pairs of fenestrations 6, 17; 7, 18; and 8, 19. In the embodiment shown, each pair of fenestrations provide a through passage through a central core of the cylindrical body 2. Each passage is separated from its neighboring passage by two turns of the external thread 3. Each pair of fenestrations are positioned adjacent to each other in an axial direction, such that an opening of a first fenestration 6 on the surface of the cylindrical body between a pair of adjacent turns of a thread on a first side of the plug, and a second fenestration 17 of the same passage has its opening positioned on the surface of the cylindrical body, between adjacent pitches of the thread on an opposite side of the plug. Since the thread follows a helical passage around the outside of the central cylindrical body, the openings of the first and second fenestrations 6, 17 of the same passage, are offset from each other axially.

In the best mode embodiment, the plug has the following dimensions:

Overall length (range) 22 mm to 30 mm;
overall length (preferred) 24 mm;
body diameter approximately 2.5 mm and preferably 2.472 mm;
length of nose 5.8 mm;
length of thread 13 mm to 13.646 mm;
thread outside diameter 4 mm;
length of drive head & collar 4.6 mm to 5 mm;

In use, the nose of the plug is engaged with the ostia of the fallopian tube or lumen. The drive end of the tool is temporarily attached to a drive tool. The drive tool incorporates an integral flexible hysteroscope, and comprises an outer sleeve housing of flexible drive rod which is adapted at one end to engage and apply torque to the rear of the elongate body of the plug. The other end of the drive rod is either manually rotatable by a surgeon, or electrically driven.

The object of the fenestrations is that tissue on either side of the fenestrations will grow into the fenestrations, meeting each other, and forming an internal band of tissue which will impede or reduce the tendency for the plug to displace from its originally implanted position in the fallopian tube. The plug may become anchored in place by the growth of tissue in the fenestrations.

Female sterilization using the occlusive plug may be a reversible operation. By attaching an applicator to the end of the plug, using the bayonet type fixing, the plug may be rotated in an anti-clockwise direction, so that the screw thread winds the plug out of the fallopian tube. There will be severance of any tissue that may have grown into or through the fenestrations during the time when the plug is in situ in the patient. However the cornu region around the ostium has substantial regenerative capacity and so any trauma caused by removal of the plug is repairable by the body. The plug will become dislodged in to the lumen of the uterine cavity of the womb, from where it may be removed via the neck of the womb. The healing should result in a patent lumen, in other words, a hole that will conduct sperm and fertilized egg.

The plug is screwed into the fallopian tube up to the point that the collar 12 meets the ostium. However, rotating the plug beyond that point may create compression on the tissue adjacent the collar which may prevent any trivial bleeding which may have occurred during insertion of the plug.

The lining of the fallopian tube, known as the endosalpinx is cut into by the thread of the plug. The endosalpinx is friable and easily to cut into. This slightly traumatizes the tissue and causes fluid generation which will help regenerative tissue enter the fenestrations.

The best mode embodiment shown has a right hand thread, although the invention encompasses embodiments having a left hand thread.

PREFERRED OR OPTIONAL FEATURES OF THE INVENTION

The fenestrations extend radially into the body.
The fenestrations are blind holes.
Two fenestrations 180° apart, but axially spaced along the body, are provided.
The 180° opposed fenestrations intersect at mutually adjacent sides.
Each passage comprising a pair of fenestrations has a depth of 1.75 mm.
The fenestrations of a passage have an overlapping portion within the body of length 1 mm.
Each fenestration has a width of 0.53 mm.
Each fenestration has a height of 0.811 mm.
Single or multiple pairs of 180° fenestrations are provided.
Three pairs of axially spaced-apart fenestrations are provided along the body.
The plug is injection moulded in a rigid, inert, biocompatible grade synthetic plastic.
The synthetic plastic is polyethylene.
The fenestrations are fine holes, of approximately 1 mm diameter or less into the body.
The body is provided, at its leading end, with a coaxial extension nose.
The extension nose tapers from a leading end which has a diameter substantially less than that of the body.
The extension nose has a rounded leading end.
The extension nose has a smooth outer surface.
The plug is of overall length 2.2 cm to 3.0 cm and preferably 2.4 cm.
The plug has a body diameter, and maximum nose diameter, of 2 mm to 5 mm, preferably 2.472 mm.
The plug has a nose length of approximately 5.8 mm.
The plug has a thread length of approximately 13.6 mm.
The thread has a diameter of approximately 4 mm, and a width at the base of the thread of 0.779 mm.
The plug is formed at its trailing end as a drive head, which is adapted, in use, to be engaged by a portion of a drive tool.
The drive head has a length of approximately 5 mm.
In use, the extension/pilot nose of the plug may be engaged with the ostia of the fallopian tube/lumen to be occluded, by temporary attachment of the plug to one end of a drive tool, the latter incorporating an integral flexible hysteroscope and comprising an outer sleeve housing a flexible drive rod adapted, at one end to engage, and apply torque to, the trailing end of the elongate body of the plug, with the other end of the drive rod being manually rotatable by the surgeon, or rotated by an electric motor or electric drive means.

The invention claimed is:

1. A plug for use in occluding a fallopian tube hysteroscopically, said plug comprising:
an elongate body having an externally threaded section;
at least one passage extending through said elongate body to enable endosalpinx and muscular tissue growth through said elongate body to aid anchorage of said plug to occlude said fallopian tube;
said externally threaded section having a thread comprising a plurality of turns;
wherein:
said at least one passage is positioned in said externally threaded section and between adjacent ones of said plurality of turns of said thread.

2. The plug as claimed in claim 1, wherein said thread is non fenestrated.

3. The plug according to claim 1, wherein said at least one passage extends radially into the body.

4. The plug as claimed in claim 1, wherein said at least one passage comprises two fenestrations 180° apart axially spaced along the body.

5. The plug as claimed in claim 1, comprising a plurality of fenestrations 180° opposed to each other, wherein said at least one passage comprises a pair of fenestrations which intersect at mutually adjacent sides to form said at least one passage.

6. The plug as claimed in claim 1, comprising at least one fenestration having a depth into said elongate body of 1.65 mm to 1.85 mm.

7. The plug as claimed in claim 1, comprising at least one fenestration having a width in a range of 0.51 mm to 0.55 mm.

8. The plug as claimed in claim 1, comprising at least one fenestration having a width of 0.53 mm.

9. The plug as claimed in claim 1, comprising at least one fenestration having a height along a length of said elongate body in a range of 0.711 mm to 0.911 mm.

10. The plug as claimed in claim 1, comprising at least one fenestration having a height along a length of said elongate body of 0.811 mm.

11. The plug as claimed in claim 1, comprising at least one pair of fenestrations, wherein said fenestrations of said at least one pair of fenestrations extend 180° opposite to each other.

12. The plug as claimed in claim 1, comprising three pairs of fenestrations, said pairs of fenestrations being spaced apart from each other axially along said body.

13. The plug as claimed in claim 1, formed by injection moulding of a rigid and inert biocompatible grade synthetic plastics material.

14. The plug as claimed in claim 1, formed by injection moulding of polyethylene.

15. The plug as claimed in claim 1, comprising a plurality of fine holes of approximately 1 mm diameter or less, protruding into said body.

16. The plug as claimed in claim 1, comprising a nose, a leading end of which has a diameter substantially less than a diameter of said body, said nose tapering outwardly towards said body.

17. The plug as claimed in claim 1, comprising a nose which has a rounded leading end.

18. The plug as claimed in claim 1, comprising a nose having a smooth outer surface.

19. The plug as claimed in claim 1, having an overall length in a range 2.2 cm to 3.0 cm.

20. The plug as claimed in claim 1, having an overall length of 2.4 cm.

21. The plug as claimed in claim 1, having a maximum body diameter in a range 2 mm to 5 mm.

22. The plug as claimed in claim 1, having a maximum body diameter of 2.472 mm.

23. The plug as claimed in claim 1, having a nose length in a range 5.4 mm to 6.2 mm.

24. The plug as claimed in claim 1, having a nose length of 5.8 mm.

25. The plug as claimed in claim 1, said thread having a length in a range of 13.2 mm to 14.0 mm.

26. The plug as claimed in claim 1, said thread having a length of 13.6 mm.

27. The plug as claimed in claim 1, said thread having an outside thread diameter in a range of 3 mm to 5 mm.

28. The plug as claimed in claim 1, said thread having an outside thread diameter of 4 mm.

29. The plug as claimed in claim 1, further comprising a drive head, said drive hearing being adapted in use to be engaged by a portion of drive tool for driving the plug along a fallopian tube.

30. The plug as claimed in claim 1, further comprising a drive head which is adapted in use to be engaged by a portion of a drive tool for driving the plug in a first rotational direction for inserting said plug along a fallopian tube, wherein said drive head is adapted to be driven by said drive tool in an opposite rotational direction, for removal of said plug.

31. The plug as claimed in claim 1, further comprising a drive head which is adapted in use to be engaged by a portion of drive tool for driving the plug along a fallopian tube wherein said drive head has a length in a range of 4 mm to 6 mm.

32. The plug as claimed in claim 1, further comprising a drive head which is adapted in use to be engaged by a portion of a drive tool for driving said plug along the fallopian tube, wherein said drive head has a length of 5 mm.

33. The plug as claimed in claim 1, having a drive head comprising a bayonet type fixing.

34. A plug for use in occluding a fallopian tube hysteroscopically, said plug comprising:
   a body having a direction of elongation, said body having an external thread comprising a plurality of turns;
   at least one passage positioned between adjacent turns of said thread and extending in said body in a direction transverse to the direction of elongation, said at least one passage enabling endosalpinx and muscular tissue growth to aid anchorage of said plug to occlude said fallopian tube.

35. A plug for use in occluding a fallopian tube hysteroscopically, said plug comprising:
   a body having a direction of elongation, said body having a non-fenestrated external thread comprising a plurality of turns;
   at least one passage positioned between adjacent turns of said non-fenestrated thread.

\* \* \* \* \*